(12) United States Patent
Mason et al.

(10) Patent No.: US 9,084,565 B2
(45) Date of Patent: Jul. 21, 2015

(54) HAND-FUNCTION THERAPY SYSTEM WITH SENSORY ISOLATION

(75) Inventors: Andrea H. Mason, Fitchburg, WI (US); Leigh A. Mrotek Gorzek, Oconomowoc, WI (US); David M. Kettner, Greenville, WI (US)

(73) Assignees: Wisconsin Alumni Research Foundation, Madison, WI (US); Wisys Technology Foundation, Madison, WI (US); Fused Innovation, LLC., Nennah, WI (US)

( * ) Notice: Subject to any disclaimer, the term of this patent is extended or adjusted under 35 U.S.C. 154(b) by 401 days.

(21) Appl. No.: 13/561,537

(22) Filed: Jul. 30, 2012

(65) Prior Publication Data

US 2013/0035612 A1 Feb. 7, 2013

Related U.S. Application Data

(60) Provisional application No. 61/513,323, filed on Jul. 29, 2011.

(51) Int. Cl.
*A61B 5/11* (2006.01)
(52) U.S. Cl.
CPC .............. *A61B 5/1124* (2013.01); *A61B 5/1128* (2013.01); *A61B 5/11* (2013.01); *A61B 5/1125* (2013.01)

(58) Field of Classification Search
CPC ................... A61B 5/11; A61B 5/1101; A61B 5/1123–5/1125; A61N 1/36103; A61N 1/36132
USPC ................ 600/587, 595; 423/247, 258; 482/4
See application file for complete search history.

(56) References Cited

U.S. PATENT DOCUMENTS

| | | | | |
|---|---|---|---|---|
| 6,625,299 | B1 * | 9/2003 | Meisner et al. | 382/103 |
| 2003/0030597 | A1 * | 2/2003 | Geist | 345/8 |
| 2008/0150891 | A1 * | 6/2008 | Berkley et al. | 345/156 |
| 2008/0234074 | A1 * | 9/2008 | Docherty | 473/451 |
| 2009/0147991 | A1 * | 6/2009 | Chau | 382/103 |

* cited by examiner

*Primary Examiner* — Max Hindenburg
(74) *Attorney, Agent, or Firm* — Boyle Fredrickson, S.C.

(57) ABSTRACT

The invention relates to rehabilitation systems and methods for providing therapy to individuals who have suffered a stroke or other neurological insult. A rehabilitation system may comprise a depth sensing camera positioned to view a workspace into which a patient's hands may be located, a display system viewable by the patient, and an electronic computer executing a stored program to display a representation of a virtual space holding at least one virtual object, display a representation of at least one hand of the patient, and monitor a virtual manipulation of the virtual object by the patient's hand. Other embodiments may include virtual reality goggles, head motion tracking, various exercises and of varying difficulty, tracking metrics and recording for subsequent playback.

24 Claims, 6 Drawing Sheets

HAND-FUNCTION THERAPY SYSTEM WITH SENSORY ISOLATION

CROSS REFERENCE TO RELATED APPLICATION

This application claims a benefit of priority under 35 USC §119 based on provisional patent application No. 61/513,323, filed on Jul. 29, 2011, the entire contents of which are hereby expressly incorporated by reference into the present application.

BACKGROUND OF THE INVENTION

The present invention relates to rehabilitation systems and methods for providing therapy to individuals who have suffered a stroke or other neurological insult and in particular to rehabilitation systems and methods for hand function.

Current research has confirmed that the adult brain is capable of extensive plastic changes after injury accommodating changes in its motor and sensory experience. Retraining of the brain thus promises stroke victims the possibility of regaining the ability to perform many daily activities.

Current devices for rehabilitation may provide for physical manipulation of a training device such as a freestanding blocks or puzzles or an instrumented exoskeleton type device. Some virtual reality devices provide for improving strength or function of muscles of larger joints of the body by tracking movement of those joints with a camera like device and displaying the results on a computer monitor.

SUMMARY OF THE INVENTION

The present inventors have recognized that abstracting rehabilitation tasks from the physical environment can provide significant benefits in rehabilitation. These benefits include the ability to make imperceptible changes in the difficulty of the rehabilitation task to challenge the patient without discouraging the patient and to properly tailor the challenge level to the patient, the ability to break the rehabilitation task into elemental components that can be individually practiced and evaluated and to use elemental rehabilitation tasks that might not be physically realizable, and the ability to implement complex schedules of different tasks and challenge levels to optimize rehabilitation. In this regard, the present invention provides a virtual reality environment that provides simulations of physical structures and a representation of the patient's hands to allow virtual manipulation of the structures in rehabilitation tasks. The patient's performance level may be monitored during these tasks to provide detailed understanding of his or her progress, to adjust the task complexity, and to provide optimization of the rehabilitation program.

The invention isolates the hand-eye control path, eliminating other possibly ambiguous or confusing sensory cues. The use of the virtual environment provides fine-grained control of the level of difficulty of the manipulation problem to sustain patient interest and maximize rehabilitative effort.

Particular features and advantages may apply to only some embodiments falling within the claims and thus do not define the scope of the invention. The following description and Figs. illustrate a preferred embodiment of the invention. Such an embodiment does not necessarily represent the full scope of the invention, however. Furthermore, some embodiments may include only parts of a preferred embodiment. Therefore, reference must be made to the claims for interpreting the scope of the invention.

DETAILED DESCRIPTION OF THE PREFERRED EMBODIMENT

Figure 1:
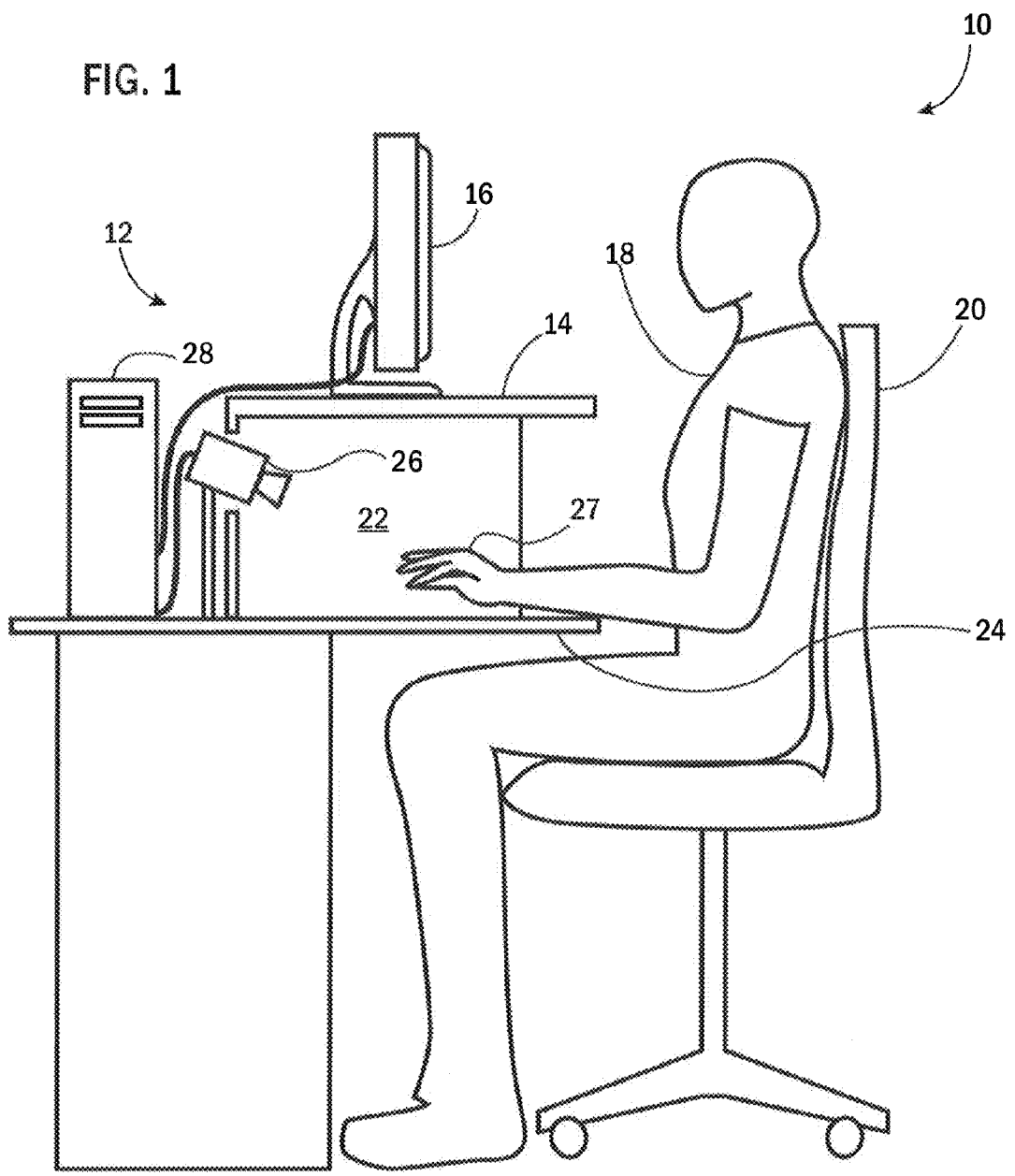
FIG. 1 is a side elevational view of an implementation of the present invention in a desk unit showing a workspace optionally shielded from the users direct vision monitored by a depth sensing camera and supporting a monitor in the patient's vision field.

Referring now to FIG. 1, a rehabilitation system 10 of the present invention may provide for example a desktop unit 12 having an upper platform 14 supporting a computer monitor 16 (for example an LCD display) for viewing by a patient 18 seated on a chair 20 or the like in front of the desk unit 12. A workspace 22 positioned beneath the upper platform 14 optionally shielded from vision of the patient 18 may be bounded by a lower platform 24 and the lower surface of the upper platform 14. A depth sensing camera 26 may be attached to view the patient's hands 27 when placed in the workspace 22 and provide a fine-grained resolution indicating hand position and finger position of the patient's hands. A depth sensing camera believed to be suitable for the present invention is available commercially from PrimeSense of Tel Aviv, Israel. Other examples of depth sensing cameras may include Microsoft Kinect commercially available from Microsoft Corporation of Redmond, Wash. and Leap Motion cameras commercially available from Leap Motion of San Francisco, Calif.

The camera 26 and display 16 may communicate with a computer 28 executing a stored program as will be described.

Figure 2:
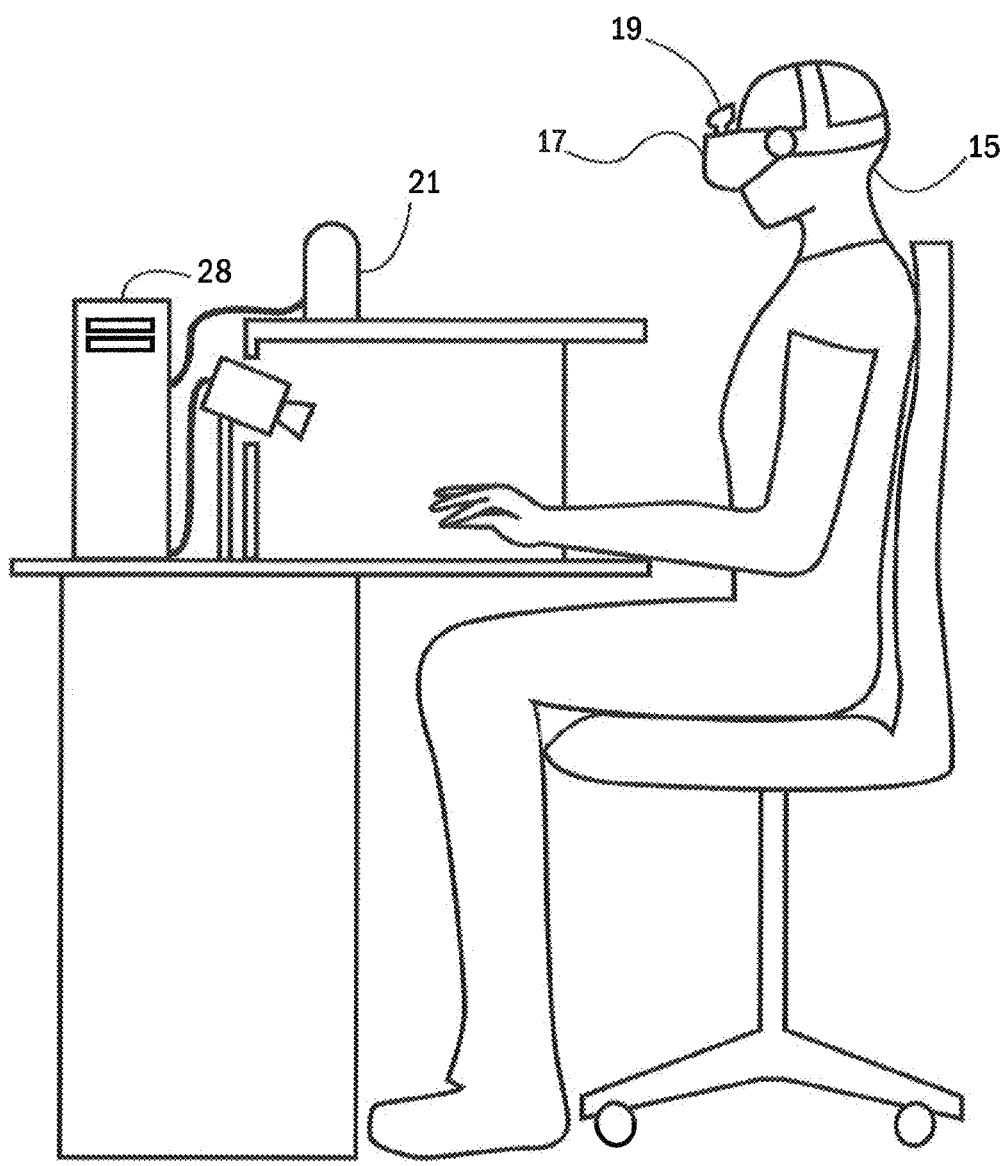
FIG. 2 is a fragmentary side elevational view similar to that of FIG. 1 showing the use of virtual reality goggles and head tracking.

In an alternative embodiment depicted in FIG. 2, the display 10 may be replaced by virtual reality goggles 17 which may be worn directly on the head of the patient 18 to receive data from the computer 28. The system also provides a head motion tracking unit 19 working with the stationary beacon 21 to relay a signal to the computer 28 indicating the position of the patient's head 15 to provide for correction of the image displayed on the goggles 17 commensurate with that which would be in the field of view of the patient with the head movement were the patient immersed in the virtual reality space 30. Head tracking virtual-reality goggles are commercially available for example, from Vuzix Corporation of Rochester, N.Y.

Figure 3:
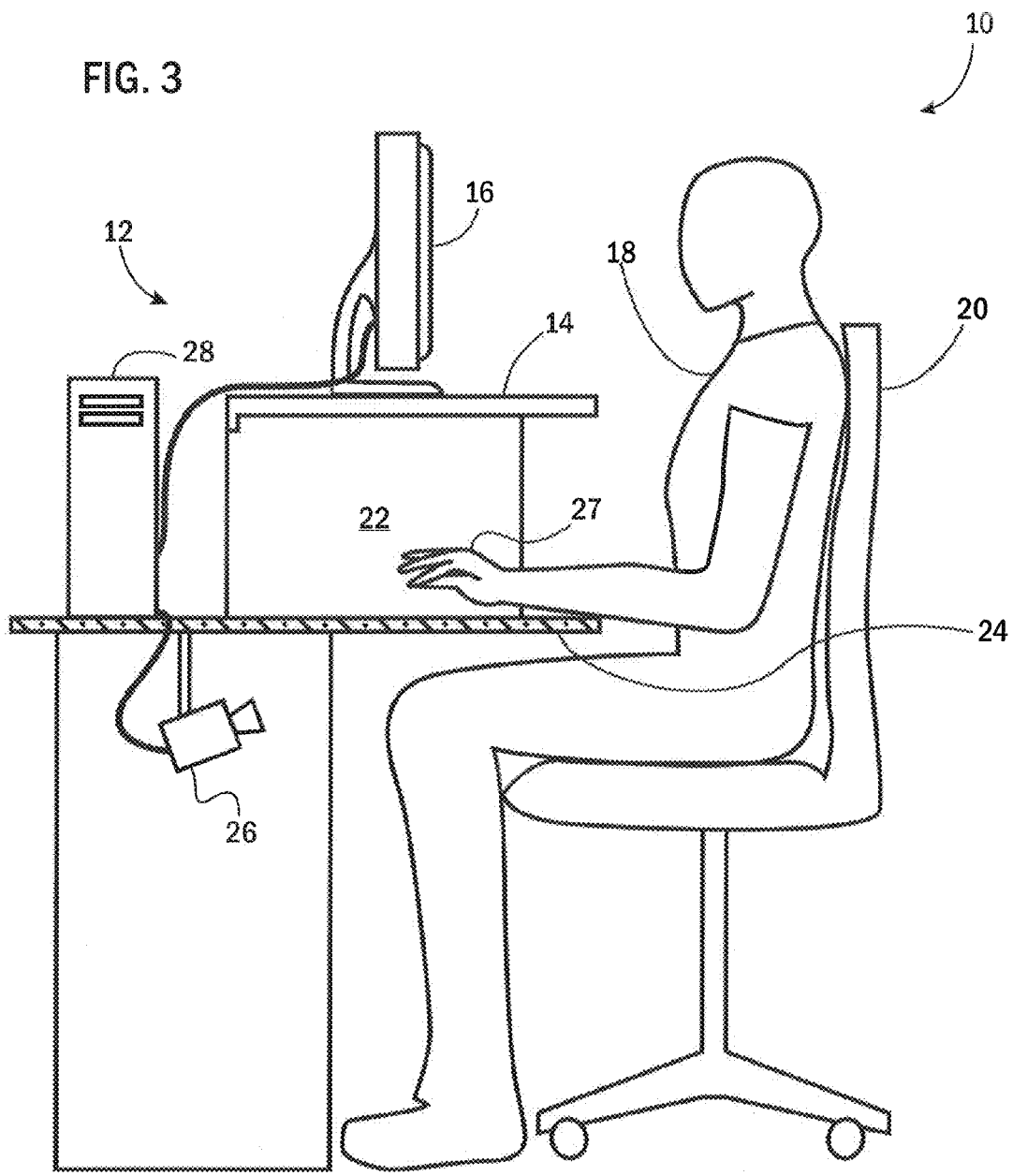
FIG. 3 is a fragmentary side elevational view similar to that of FIG. 1 showing the workspace monitored by the depth sensing camera positioned below the workspace.

In an alternative embodiment depicted in FIG. 3, the camera 26 may be attached below the workspace 22, instead of above as shown in FIG. 1, to view the patient's hands 27 when placed in the workspace 22. In this arrangement, the surface of the workspace may be a transparent material, such as glass, allowing the camera to view the workspace through the surface or the surface of the workspace may be removed.

Figure 4:
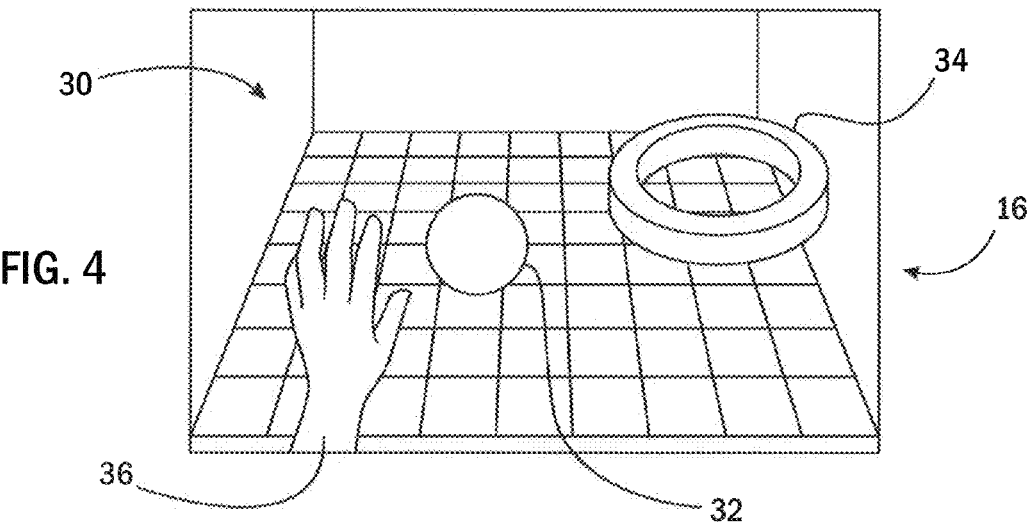
FIGS. 4 and 4a-e are screen displays showing images on the monitor presenting manipulation tasks to the patient using virtual items positioned with respect to virtual representations of the patient's hands and fingers.

Referring now to FIG. 4, the computer 28 may provide a display of a virtual space 30 depicted in two dimensions on the display 16 including one or more virtual objects such as a ball 32 and hoop 34. Each of these virtual objects 32 and 34 will have a defined location in the virtual space stored as a mathematical representation and a defined shape (outer periphery) and orientation. The program executing on the computer 28 may read information from the depth sensing camera 26 to reconstruct a virtual hand 36 in the display and to translate the actual hand location, orientation, and finger positions of the patient's hand, using a predetermined mapping, to the virtual space 30 so that the hand 36 may be displayed relative to the objects 32 and 34. Typically such mapping will center the virtual space 30 with respect to the workspace 22 and will give each corresponding dimensions and orientation. By establishing the location of the patient's hand as a virtual hand 36 in virtual space 30 and knowing finger positions, the patient may manipulate the virtual objects 32 and 34 by causing the virtual hand 36 to grasp the objects and allowing them to be moved with respect to each other. Although the present invention does not contemplate any haptic feedback to the patient with respect to the grasping action, the virtual objects 32, 34 and 36 will observe correct collisional physics preventing them from moving through each other. The orientation of the objects 32 and 34 may be changed or fixed according to the particular puzzle problem. It should be emphasized, however, that the correct collisional physics may also be disabled to simplify the tasks and to isolate or amplify problems the patient may be experiencing.

Figure 5:
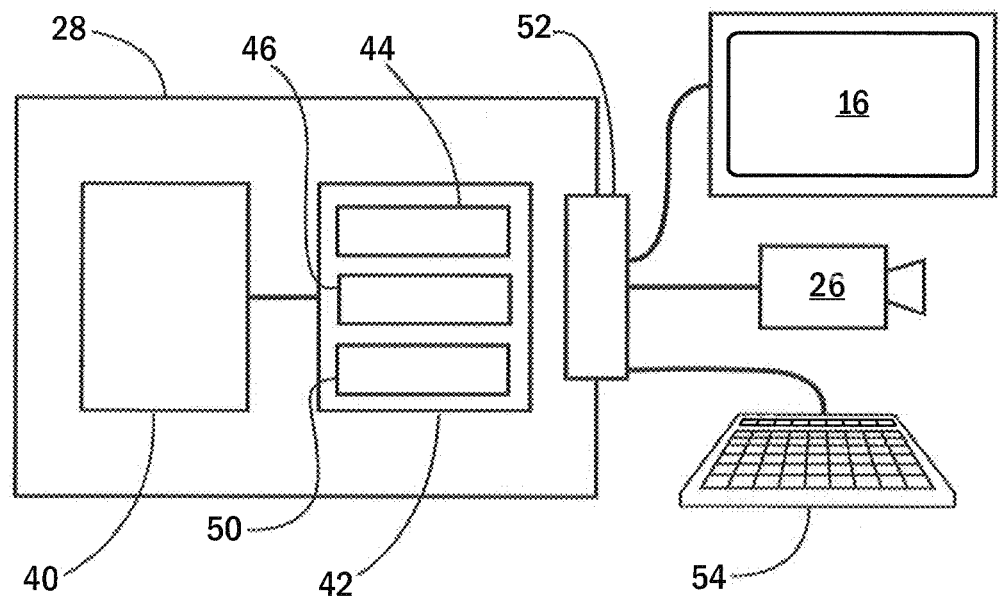
FIG. 5 is a function block diagram of the present invention as may be implemented on a electronic computer.

Referring now to FIG. 5, the computer 28 may include a processor 40 communicating with the memory 42 containing an operating system 44 and one or more application programs 46 as will be described that may be executed by the electronic computer. The memory may also hold a data table 50 for storing patient metrics for review by physical therapist or the like. The computer 28 may provide for an interface 52 communicating with the display 16 and the camera 26 according to techniques well known in the art. A keyboard or other user input device 54 may also be provided for initialization and starting of the program.

Figure 4A:
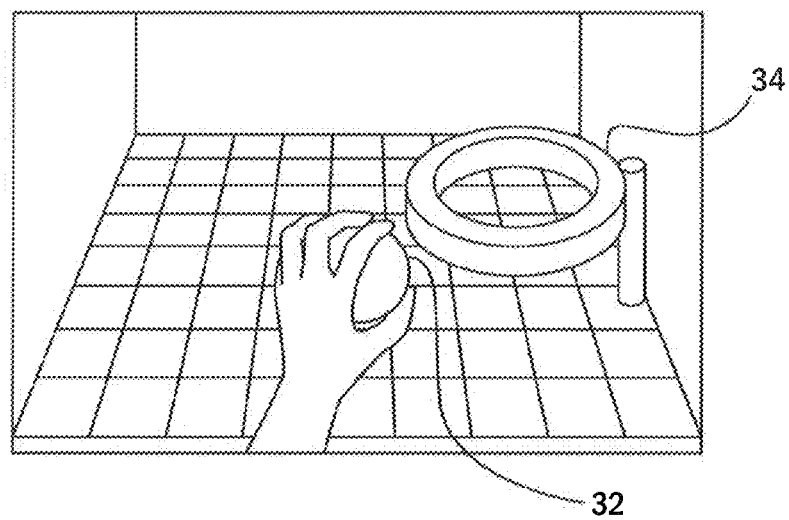

In the depiction of FIG. 4a, the patient may grasp the ball 32 and pass it through the hoop 34 with the hoop 34 being maintained stationary and the hand blocked by physical structure of the hoop 34 or allowed to pass through the hoop 34 with the ball 32 not being allowed to pass through the physical structure of the hoop 34 but only through the opening in the hoop 34 or outside of the loop entirely.

Figure 4B:
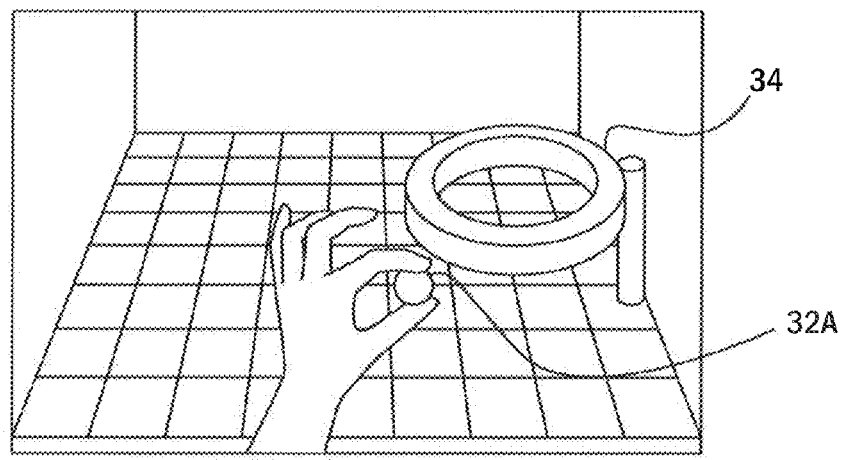

In the depiction of FIG. 4b, the ball 32a has been decreased in size so that the patient must switch from a power grip to a precision grip in order to move the smaller object through the opening of the fixed hoop 34.

Figure 4C:
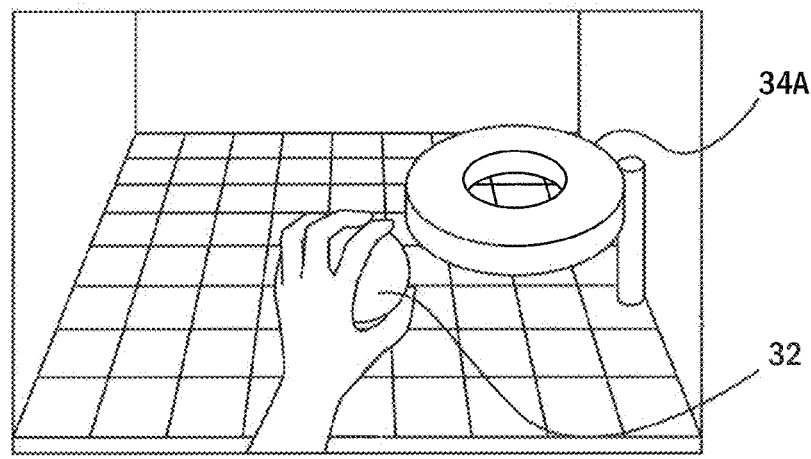

In the depiction of FIG. 4c, the opening of the fixed hoop 34a has been decreased in size so that greater precision of motion is required for the patient to maneuver the ball 32 through the hoop 34a.

Figure 4D:
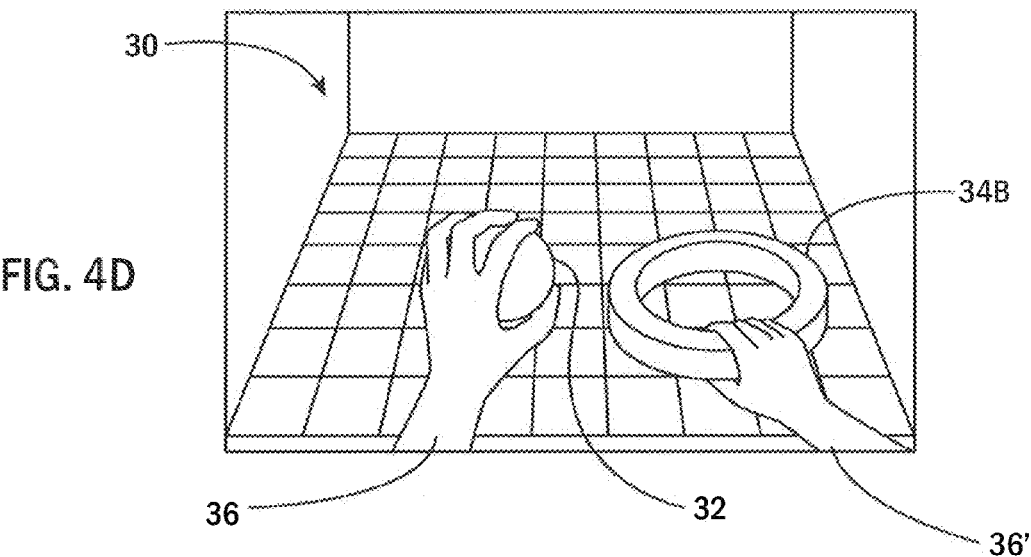

In the depiction of FIG. 4d, the hoop 34b is no longer fixed but must also be grasped by the patient using a second virtual hand 36'. Thus the patient must control both ball 32 and hoop 34b in virtual space 30 in order to maneuver the ball 32 through the opening of hoop 34b.

Figure 4E:
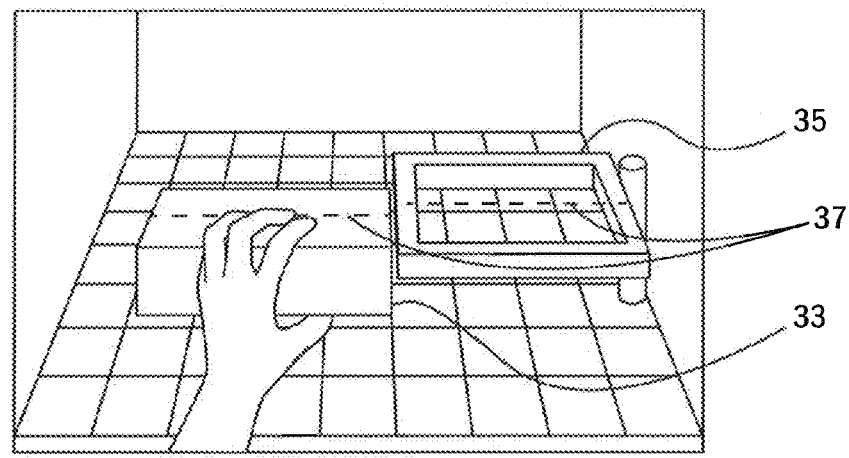

In the depiction of FIG. 4e, the virtual objects consist of a rectangular prism 33 and rectangular hoop 35. The rectangular hoop 35 may be stationary or moveable. The patient must move the prism 33 through the hoop 35, but as prism 33 cannot pass through the physical structure of hoop 35 the orientations 37 of the virtual objects 33 and 35 must be considered to complete the task.

Significantly, the changes in the difficulty of the task, for example, changing the size of the opening in the fixed hoop 34a or the size of the ball 32a may be very gradually changed to be imperceptible to the patient allowing the task difficulty to be smoothly adjusted, for example, in response to changes in patient skill level. As will be described below, this change may be driven by a performance metric measuring how well the patient performs the task. Alternatively, the changes in difficulty and in fact the tasks themselves may be adjusted according to a predetermined schedule executed by the computer to optimize the rehabilitation according to empirical information derived from the system or elsewhere. Such a schedule may for example continuously change the difficulty to increase or decrease it, but more typically may alter tasks and difficulty levels both up and down in a pattern as may be determined to be therapeutically most effective.

Various exercises, including such as these described in FIGS. 4a-4e, may essentially be performed in a virtual environment to simulate activities of daily living. The present invention importantly allows the activities of daily living to be broken into elemental tasks without regard to physical constraints. So, for example, an activity of daily living may be picking up a glass while retaining the orientation of the glass vertically and moving it to set it on a different surface. This task can be broken into the tasks of: (a) grasping, (b) maintaining an orientation, (c) moving an object between two locations, and (d) releasing an object placed on a surface. With actual physical structures, these different tasks are inextricably linked, however, in the virtual environment each can be dealt with separately. For example, a virtual glass may automatically maintain correct orientation independent of the patient's hand so that the patient may work on task (c) without the distraction of task (b). Further the patient's ability with task (c), thus isolated, can be accurately measured. Whereas with physical structure, practicing releasing an object (d) necessarily requires completion of each of tasks (a)-(c), this is not necessarily true with the virtual environment where, for example, a glass may be initialized to be "attached" to and thus grasped by the patient's hand. Each of these separate tasks may be practiced independently or together in a sequence that emulates the everyday activity. Each of the tasks may nevertheless be independently monitored to permit reinforcement or practice of those tasks that represent the greatest challenge to the individual, in designing a therapeutic program.

In the process of designing the tasks, the physics of the environment may also be adjusted, for example, the linear or rotational inertia of one or more of the manipulated items may be independently adjusted, friction may be increased or decreased, or items may be given local attraction to periodic coordinates as with a "snap, grid".

The computer 28, program 42 and camera 26 will be constructed and organized to limit time delays to no more than approximately 16 to 33 ms in updating the position of the virtual hand 36 with respect to the objects 32 and 34.

Figure 6:
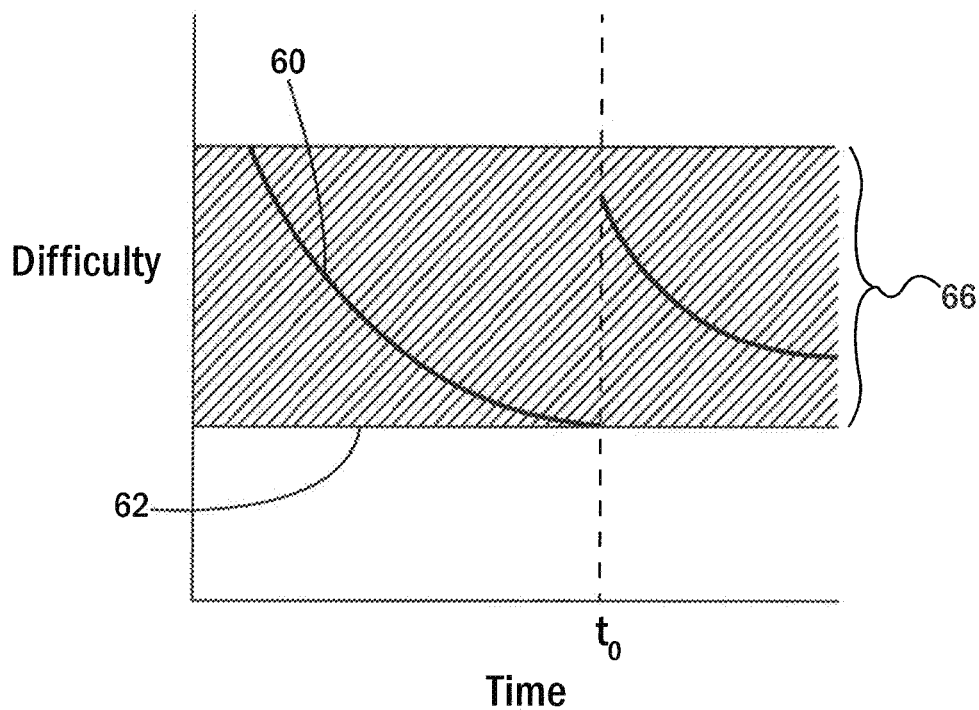
FIG. 6 is a diagram showing an improving patient metric and adjustment of the task to maintain a given challenge range.

Referring now to FIG. 6, the patient's success with the exercise of the type described with respect to FIG. 4 above may be quantified according to one or more rehabilitation metrics 60 which may be tracked over time with the data provided to a physical therapist for review if desired. This data may include the metrics or may provide for an ability to review actual screen videos of the patient's performance or may provide for other types of data with respect to the patient's performance including for example data identifying particular muscle sets that remain poorly controlled, for example, by reverse kinematics techniques. The monitoring of the rehabilitation metrics 60 may be performed with respect to a predefined interest threshold 62 to change the task assigned to the patient to increase its challenge level a time t0 to keep the challenge to the patient with in a zone 66 roughly established to maintain the patient's interest without being overly challenging for the patient such as might be discouraging. Change in the task or exercise given to the patient may be performed on extremely fine scale for example by incrementally shrinking the size of the hoop 34 to provide extremely tight control of the challenge reward of the system.

The same or different exercises may be performed one after another, in repetitions, and each exercise may have the same or a varying degree of difficulty, and in various combinations. The degree of difficulty may be set arbitrarily, to a consistent value, or in a preferred embodiment, according to one or more metrics that may be measured from one or more previous exercise. Metrics may include, for example, the total time to complete an exercise (e.g. to move the ball through the hoop), the maximum spatial distance encountered from the target while attempting the exercise (e.g. maximum distance encountered from the ball to the hoop) and/or the number of collisions encountered while attempting the exercise (e.g. number of times the ball hit the hoop). As noted above, the degree of difficulty may be varied both up and down according to a schedule as may be determined to be therapeutically valuable.

In this latter embodiment, the difficulty of the exercise (e.g. the relative size of the ball and hoop) may be adjusted according to the metric obtained from a previous attempt at completing exercise. In this way the difficulty of the exercise, for example, may remain constant at a level that is neither too easy nor frustrating to the user. As the user proficiency increases as indicated by the metric, the difficulty of the task may automatically increase as well. Limits to difficulty may be placed on the low and high sides of difficulty and the progress of the user as reflected in the measured metric may be plotted and output to a supervising healthcare worker. It will be understood that the process of changing the difficulty of the task may be substantially continuous (for example by small increments of change in hoop diameter) or may be accomplished through a changing of the tasks from simpler tasks to harder tasks or combination of both. The changing of the tasks, may for example, involve different virual objects or different required manipulations of the virtual objects, for example balancing objects on top of each other versus inserting one object through another object where orientation does not matter (e.g. ball and hoop) or where orientation does matter cylinder and cylindrical opening.

The patient may also perform each exercise at a location other than where the therapist may be monitoring the exercise, which monitoring may be communicated, for example, in real time via a local area network (LAN), wide area network (WAN) and/or the Internet. In this regard the computer 28 may be attached to the Internet using a standard interface circuit of the type well known in the art.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to "a controller" and "a processor" can be understood to include one or more controllers or processors that can communicate in a stand-alone and/or a distributed environment(s), and can thus be configured to communicate via wired or wireless communications with other processors, where such one or more processor can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties.

What is claimed is:

1. A rehabilitation system for stroke victims comprising:
   a depth sensing camera positioned to view a workspace into which a patient's hands may be located, the camera providing a. resolution allowing identification of actual hand and finger positions of the patient's hands;
   a display system viewable by the patient;
   an electronic computer executing a stored program in receiving information from the depth sensing camera to:
   (a) display on the display system a representation of a virtual space holding at least one virtual object having predefined dimensions and spatial location in the virtual space;
   (b) display a representation of at least one hand of the patient depicting a location of the hand and position of the hand and fingers in the virtual space according to a predefined mapping between actual space and virtual space;
   (c) monitor a virtual manipulation of the virtual object by the patient's hand to provide a metric indicating a performance level by the patient in manipulation of the virtual object; and
   (d) change a difficulty of a rehabilitation task requiring virtual manipulation of the virtual object by the patient's hand.

2. The rehabilitation system of claim 1 wherein the electronic computer further executes the stored program to change the difficulty of the task of virtual manipulation of the virtual object between completions of tasks.

3. The rehabilitation system of claim 2 wherein the electronic computer changes the difficulty of the task of virtual manipulation according to the metric indicating a performance level of a previous execution of the task.

4. The rehabilitation system of claim 3 wherein the computer changes the difficulty of the task of virtual manipulation to provide a substantially constant performance level by the patient.

5. The rehabilitation system of claim 3 wherein the difficulty of the task is changed by at least one of: changing dimensions of the at least one virtual object, and changing a virtual manipulation of the virtual object.

6. The rehabilitation system of claim 2 wherein the electronic computer further executes the stored program to change the difficulty of the task of virtual manipulation of the virtual object by an amount relating to a change in the patient's skill level.

7. The rehabilitation system of claim 1, wherein the metric is the amount of time to complete an exercise with the virtual object.

8. The rehabilitation system of claim 1, further comprising a shielding between the workspace and the patient adapted to shield the workspace from the patient's vision.

9. The rehabilitation system of claim 1 wherein the electronic computer further executes the stored program to permit virtual manipulation of the virtual object to emulate everyday tasks as decomposed into elemental motions that may be independently completed and monitored and wherein the monitoring provides a different metric for each of the elemental motions.

10. The rehabilitation system of claim 1, wherein the electronic computer further executes to update the location of the hand and position of the hand and fingers with respect to the virtual object less than 33 ms after corresponding movement of the patient's hand.

11. The rehabilitation system of claim 1, wherein the electronic computer farther executes to display a representation of both hands of the patient depicting a location of each hand and the position of the hands and fingers in the virtual space according to a predefined mapping between actual space and virtual space.

12. The rehabilitation system of claim 1, further comprising a plurality of virtual objects wherein the electronic computer further executes to display the virtual objects with correct collisional physics preventing them from moving through each other.

13. The rehabilitation system of claim 12, wherein the metric is selected from the group consisting of maximum spatial distance encountered from between the virtual objects and number of collisions encountered while attempting the exercise.

14. The rehabilitation system of claim 1 wherein the display system is a goggle-based display to provide a portable therapeutic device.

15. A method for providing rehabilitation for stroke victims comprising:
   providing a workspace into which a patient's hands may be located;
   displaying a virtual space representing the workspace, the virtual space holding at least one virtual object having predefined dimensions and spatial location in the virtual space;
   displaying a representation of at least one hand of the patient depicting a location of the hand and position of the hand and :fingers in the virtual space according to a predefined mapping between actual space and virtual space;
   monitoring an exercise comprising the virtual manipulation of the virtual object by the patient's hand to provide a metric indicating rehabilitative level;
   changing the virtual object in response to the metric; and
   change a difficulty of a rehabilitation task requiring virtual manipulation of the virtual object by the patient's hand.

16. The method of claim 15, wherein the metric is the amount of time to complete an exercise with the virtual object.

17. The method of claim 15, further comprising shielding the workspace from the patient's vision.

18. The method of claim 15, further comprising a plurality of virtual objects including a ball and a hoop, wherein the exercise comprises grasping the ball and passing it through the opening in the hoop.

19. The method of claim 18, wherein the size of the ball is decreased in a subsequent exercise in response to the metric.

20. The method of claim 18, wherein the size of the opening in the hoop is decreased in a subsequent exercise in response to the metric.

21. The method of claim 16, further comprising a plurality of virtual objects including a rectangular prism and a rectangular hoop, wherein the exercise comprises moving the rectangular prism through the opening in the rectangular hoop.

22. The method of claim 15, further comprising tracking a plurality of metrics for a plurality of exercises over time.

23. The method of claim 15, further comprising recording the virtual manipulation of the virtual object by the patient's hand for subsequent playback.

24. The method of claim 15, further comprising identifying particular muscle sets relating to the task.

* * * * *